United States Patent
Wiggins et al.

(10) Patent No.: US 6,849,056 B1
(45) Date of Patent: Feb. 1, 2005

(54) LOW PROFILE METACARPAL FRACTURE BRACE

(76) Inventors: Chris E. Wiggins, 3117 Beach Blvd., Pascagoula, MS (US) 39567; Tom Young, P.O. Box 1283, 3615 Hospital Rd., Pascagoula, MS (US) 39568-1283

( * ) Notice: Subject to any disclaimer, the term of this patent is extended or adjusted under 35 U.S.C. 154(b) by 121 days.

(21) Appl. No.: 10/291,993

(22) Filed: Nov. 12, 2002

(51) Int. Cl.$^7$ ................................................. A61F 5/00
(52) U.S. Cl. ............................. 602/21; 602/20; 602/63; 602/64; 128/879
(58) Field of Search ............................. 602/21, 22, 62, 602/64, 5, 20, 63, 75; 128/878, 879, 880; 2/16, 20

(56) References Cited

U.S. PATENT DOCUMENTS

| | | | | |
|---|---|---|---|---|
| 4,765,320 A | * | 8/1988 | Lindemann et al. | 602/22 |
| 4,850,341 A | * | 7/1989 | Fabry et al. | 602/21 |
| 4,953,568 A | * | 9/1990 | Theisler | 128/878 |
| 5,214,799 A | * | 6/1993 | Fabry | 2/20 |
| 5,417,645 A | * | 5/1995 | Lemmen | 602/21 |
| 5,771,901 A | * | 6/1998 | O'Brien | 128/878 |
| 5,916,186 A | * | 6/1999 | Turto et al. | 602/20 |
| 6,341,376 B1 | * | 1/2002 | Smerdon, Jr. | 2/16 |
| 6,482,168 B1 | * | 11/2002 | Betcher | 602/21 |
| 6,517,501 B1 | * | 2/2003 | Slautterback | 602/5 |
| 6,561,995 B1 | * | 5/2003 | Thibodo, Jr. | 602/22 |

* cited by examiner

Primary Examiner—Fadi H. Dahbour
(74) Attorney, Agent, or Firm—Roger A. Marrs

(57) ABSTRACT

A rigid fracture brace having a rigid and non-bendable in use U-shaped member with an inner, soft-cushioned layer carried on an outer rigid layer defining an open inner cavity for laterally receiving and supporting a user's hand, adjacent to the metacarpal grouping of hand bones. The member is of high aspect ratio and is held in position by a three strap system which includes a lower thumb strap, a middle palm strap and an upper palm strap immediately below the fingers. One end of each strap is immovably fixed to the backside of the member and securement of each strap to the member includes a loop associated with each strap. Each strap further includes a two-component hook and pile fastener so as to avoid critical registration of holes and tongs. The pile component of the fastener is carried along the backside of each strap and each strap terminates with a free-end carrying the hook component of the fastener at the tip of the inside surface of each strap. The free end of each strap is adapted to be trained through associated loops of the strapping assembly. The inventive brace extends from the base of the hypothenar eminence to beyond the fifth metacarpal-phalangeal joint to support the base of the proximal phalanx of the fifth finger.

11 Claims, 2 Drawing Sheets

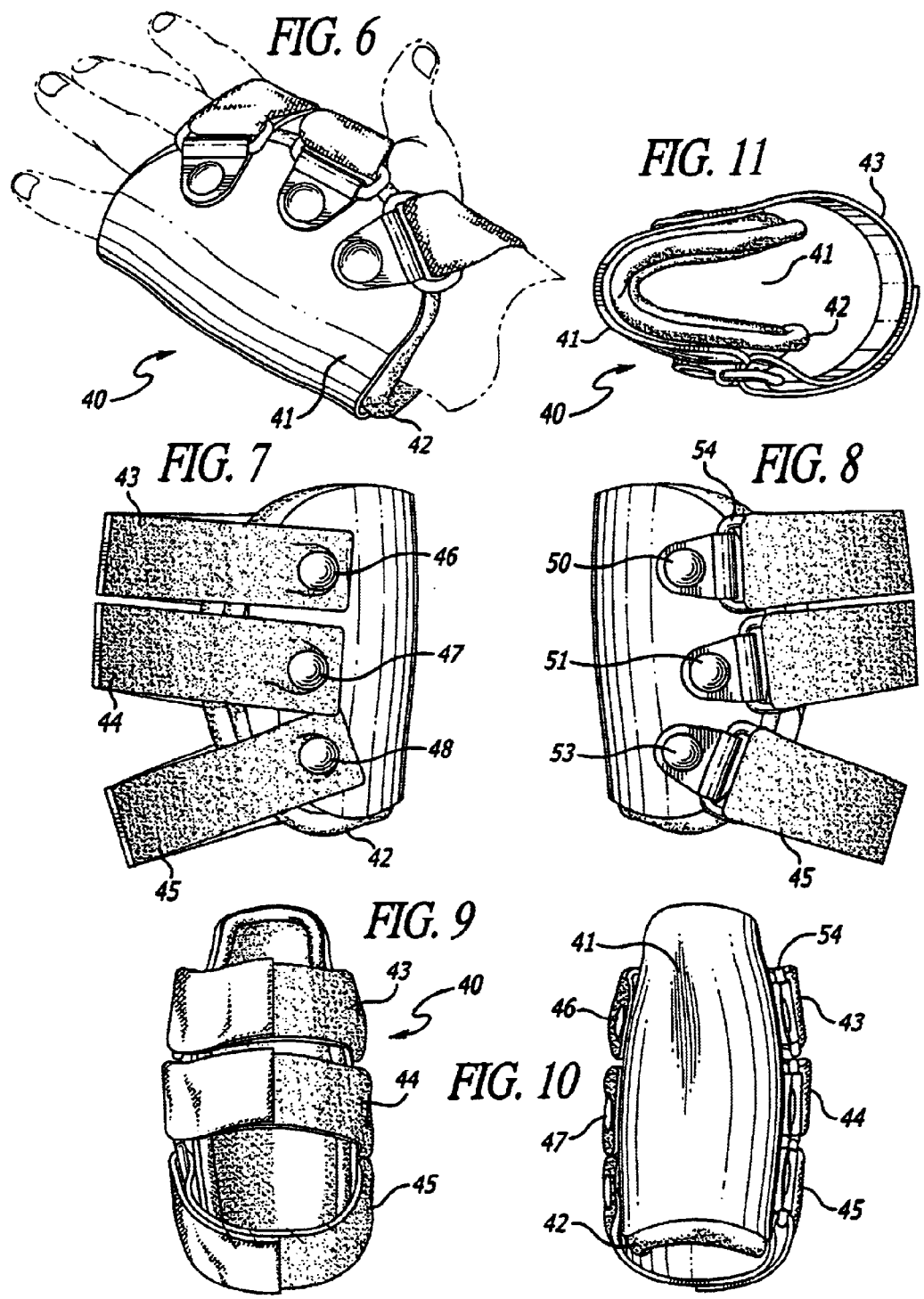

LOW PROFILE METACARPAL FRACTURE BRACE

Priority Claimed on 60-214,366 filed Jun. 28, 2000 now abandoned and Ser. No. 09-886,257 pending filed Jun. 22, 2001.

BACKGROUND OF THE INVENTION

1. Field of the Invention

The present invention relates to the field of medical braces for fractures involving bones of the hand and more particularly to a brace for immobilizing fractures of metacarpal bones while allowing some freedom of finger movement.

2. Brief Description of the Prior Art

Conventionally, when fractures of hand bones occur, physicians generally employ immobilization using traditional methods such as employing casts or splints. This is particularly traditional for treating fourth and fifth metacarpal fractures of hand bones. Such traditional methods greatly restrict movement of the fingers and thereby increase the likelihood of joint stiffness. Furthermore, casts or splints greatly restrict active lifestyles and are not suited to be worn in sporting or industrial settings. Also, conventional casts or splints greatly reduce the ability of a patient to bathe because the cast or splints are not readily removable.

Other attempts to provide a suitable splint or brace include an adjustable splint, as disclosure in U.S. Pat. No. 3,124,127. This Patent discloses an "adjustable" splint, which is composed of a bendable material that is manually bent about the side of the hand. The bendable adjustment in use does not provide support beyond the fifth metacarpal phalangeal joint of the user's hand. The disclosed splint is short or limited in length so as to fail to support the base of the proximal phalanx of the fifth finger. Furthermore, since the splint is "bendable", the splint may not hold its shape or adjustment when deformed about the user's hand.

The disclosure in U.S. Pat. No. 3,124,127 illustrates and describes a soft, bendable metal piece intended to hold the fracture in place in cooperation with only two straps and buckles. Such an arrangement causes tissue damage and development of ulcerations under the splint. Since the splint is bendable, deformable or pliable, looseness of the metal piece occurs causing rubbing between the skin and the inside of the splint, regardless of strap tightness.

Additionally, the straps are affixed to the bendable piece by pivots which permits movement of the straps relative to the bendable piece rendering the splint unstable and movable, which lessens support for the fracture.

It is essential in the splint of U.S. Pat. No. 3,124,127 that the metal 20 or 21 be "bent" or deformed on situ or in use when applying the splint to the user's hand. Since the material is bendable, the bendability of the metal piece is still present after the splint has been installed, which results in poor support for the fracture.

Therefore, a long-standing need has existed to provide a rigid and non-bendable fracture brace which is more convenient for a physician to apply than other traditional splints, particularly for treating fourth and fifth metacarpal fractures. The rigid and non-bendable fracture brace should be designed to immobilize fractures of the metacarpals and should have a low profile, so that the brace may be employed in active lifestyles and is suitably removable for patient bathing. Once applied to the user's hand, the brace must be stable, rigid and non-bendable.

SUMMARY OF THE INVENTION

Accordingly, the above problems and difficulties are avoided by the present invention which provides a fracture brace having a rigid and non-bendable U-shaped member with an inner, soft-cushioned layer carried on an outer rigid layer defining an open inner cavity for insertably receiving and supporting a lateral portion of the user's hand, adjacent to the metacarpal grouping of hand bones. The rigid and non-bendable member is held in position by a strapping system which includes a lower thumb strap, a middle palm strap and an upper palm strap immediately below the fingers. One end of each strap is fixly secured to the backside of the U-shaped member in a non-pivoting relationship and the system includes a loop associated with each strap for conducting a fixed end of each strap therethrough. Each strap further includes a two-component hook and pile fastener or connection. The pile component of the fastener is carried along the backside of each strap and each strap terminates with a free-end carrying the second or hook component of the fastener at the tip of the inside surface of each strap. The free end of each strap is adapted to be trained through associated loops at the fixed end of the strapping assembly. The rigid U-shaped member has a length which encompasses not only the fifth, but also the fourth, metacarpal phalangeal joint. The inventive brace extends from the base of the hypothenar eminence to beyond the fifth metacarpal-phalangeal joint to support the base of the proximal phalanx of the fifth finger. The rigid and non-bendable brace member is maintained in a stable and non-adjusting position by the three-strap assembly having fixly secured fasteners, not pivots, which runs transversely around the hand.

Therefore, it is among the primary objects of the present invention to provide a low-profile, stable metacarpal fracture brace which will not bend or deform so as to readily immobilize fractures of the fourth metacarpal and the fifth metacarpal in particular, while permitting limited movement of the fingers.

Another object of the present invention is to provide a rigid, non-bendable and non-deformable fracture brace for protecting the metacarpals of the hand which is removably held in position by a three-strap assembly while allowing finger movement and which can readily be removed by the person wearing the brace for bathing purposes.

Yet another object of the present invention is to provide a rigid, low profile metacarpal fracture brace which allows more freedom of motion of the fingers than is conventionally available using conventional casts or splints, thereby decreasing the likelihood of joint stiffness.

A further object resides in providing a low profile for a rigid fracture brace worn on the hand which will allow the wearer or patient to engage in active lifestyles and it is particularly suited to be worn in sporting and industrial settings.

Yet another object resides in providing a stiff, rigid, and non-bendable brace for immovably supporting the lateral portion of a user's hand, which is pre-formed in manufacture, and resulting in a non-bendable U-shaped member that is rigid in use and rigid when applied to the hand of the user.

An object also resides in a rigid brace held in place on the hand of the user which comprises a three-strap arrangement wherein the ends of each strap are fixly attached in a non-movable or non-pivoting relationship with respect to a rigid U-shaped member.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 6 is a perspective view of another embodiment of the present invention illustrating the rigid and non-bendable brace;

FIG. 7 is a side elevational view of the embodiment shown in FIG. 6;

FIG. 8 is a side elevational view taken from the opposite side from that shown in FIG. 7;

FIG. 9 is a front view of the rigid and non-bendable brace shown in FIGS. 6–11;

FIG. 10 is a back view thereof; and

FIG. 11 is a top plan view of the rigid and non-bendable brace.

BRIEF DESCRIPTION OF PREFERRED EMBODIMENT

Figure 1:
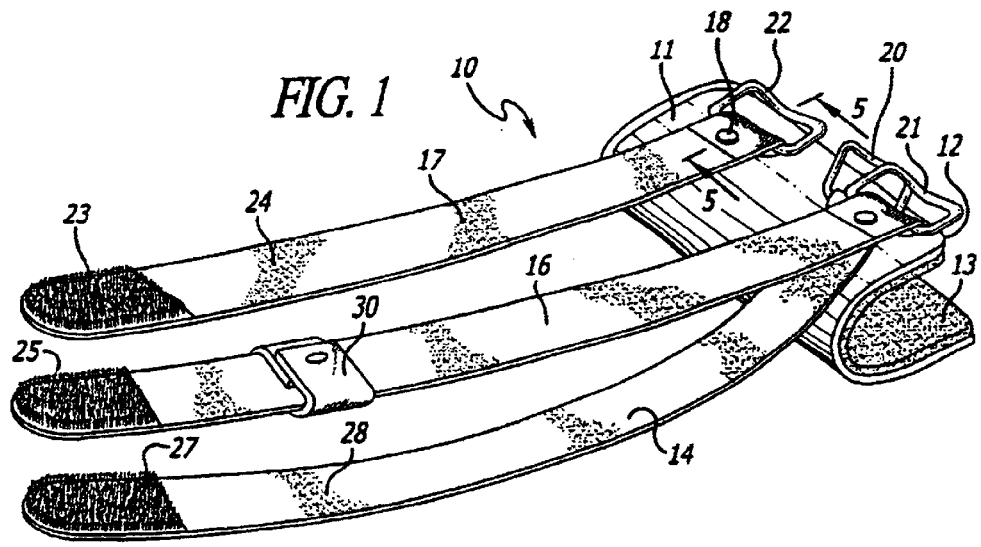
FIG. 1 is a prospective view of a novel rigid and non-bendable low profile metacarpal fracture brace incorporating the present invention illustrating the necessary three-strap assembly laid out preparatory for placing the rigid brace on the lateral portion of a fractured hand of the user.
Figure 4:
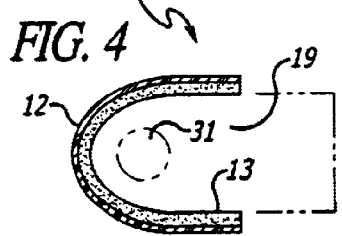
FIG. 4 is an enlarged transverse cross-sectional view of the rigid fracture brace shown in FIG. 3 as taken in the direction of arrows 4—4 thereof.

Referring to FIG. 1, the novel low profile metacarpal brace as illustrated in the general direction of arrow 10 which includes a rigid and non-bendable brace member 11 formed with a U-shaped cross section and which includes an outer rigid and non-bendable layer or shell of plastic or plastic-like material and an inner layer of soft, cushioned material. The outer rigid layer or shell is indicated by numeral 12, as shown in FIG. 4, while the soft inner layer is indicated by numeral 13. An opening or cavity 19 extending along the length of the member 11 is used for inserting the fractured hand of the user, preparatory for wrapping the hand and brace member with the strap assembly.

It is important and critical to the use of the invention that the side or lateral portion of the user's hand is inserted into the opening defined by the opposing inner surface of the cushion lined shell. The elongated opening 19 has an entrance leading into the opening or cavity for insertably receiving the user's hand.

The outer rigid layer or shell is rigid, as meaning non-bendable, in use. The layer or shell is manufactured from a hard, rigid material so that receiving cavity 19 is defined prior to use. In use, the layer or shell 12 is rigid as defined by the definition set forth in Webster's New World Dictionary, Second College Edition, published by Simon and Schuster, having Library of Congress No. 0-671-41809-2, cl., indexed. Page 1226 defines "rigid" as "1. Not bending or flexible, unyielding; stiff and hard (a rigid metal girder). 2. Not moving, firmly fixed." Rigid layer or shell 12 maintains its shape and will not bend once applied to the hand of the user. The rigid brace is not intended nor desired to bend during fitting onto the user's hand and certainly the layer or shell must not bend or yield once installed on the hand. Prior splints employ soft, pliable and bendable components which yield or bend when the user moves his hand, which re-configures or adjusts the splint which causes rubbing between the skin and the splint. This friction or rubbing causes ulcerations and sores.

The strap assembly includes three straps, wherein one end of each strap is fixly secured to the member 11. For example, a thumb strap 14 has one end selected for non-pivotal, fixed attachment to the brace member shell 12 by means of a non-pivotal, fixed rivet 15 that is used in order to retain one end of a mid or palm strap 16. An end of an upper palm strap 17 is attached to the member 11 by a separate, non-pivoting rivet 18. It is to be particularity noted that each of the respective ends which are secured to the member 11 are also formed in a fold about and around attachment loops. For example, attachment loop 20 is carried at the end strap 14 while loop 21 is carried at the end of strap 16. Loop 22 is carried on the end of strap 17. The loops are retained by the non-pivotal fixed rivets 15 and 16. The fixed loops are intended to insertably receive the free ends of the respective straps after the straps have been wrapped around the member 11 and the injured or fractured hand of the user. For example, end 23 of the upper or top strap 17 is provided with one component of a two-component fastener and is identified by numeral 23 and is intended to be inserted through the loop 22 and folded over the rung of the loop for attachment to a second component of the two-component fastener which is carried on the outer surface of strap 17 and is indicated by numeral 24. The two-component fastener is of a hook and pile type so that an adjustable fit can readily be achieved without having to align fastener components, such as is required by conventional buckles or the like. The fastener component 23 may be of a hook construction while the pile construction 24 is placed along the entire length of the strap from the component 23 to the fastener 18. This construction is illustrated more clearly in FIG. 5. It is to be understood that straps 14 and 16 are constructed in the same manner as described with respect to strap 17 and fasten in a similar manner in that the free end of strap 16 carrying a first component 25 is passed through loop 20 and folded over for attachment with the second component of the hook and pile fastener as indicated by numeral 26. With respect to strap 14, the free end carrying the first fastening component 27 is passed through loop 21 and folded over the rung of the loop for attachment to the second component 28 carried on the outside of strap 14.

Each of the respective straps 14, 16 and 17 are composed of a cloth or fabric material with the first and second components of the two-component fastener carried on the outside surfaces of the strap material. The straps are flexible and are soft without skin damaging edges so as not to cause discomfort when the straps are wound about the brace member 11 and the hand of the user.

The mid-palm strap 16 may carry a spacer cushion member 30 which may be detachably connected to the strap 16 and may be slid along the mid-section of the strap to a desired location. It is intended that member 30, if used, be placed between the thumb and index finger of the user when the strap assembly has been fastened.

Figures 2, 3:
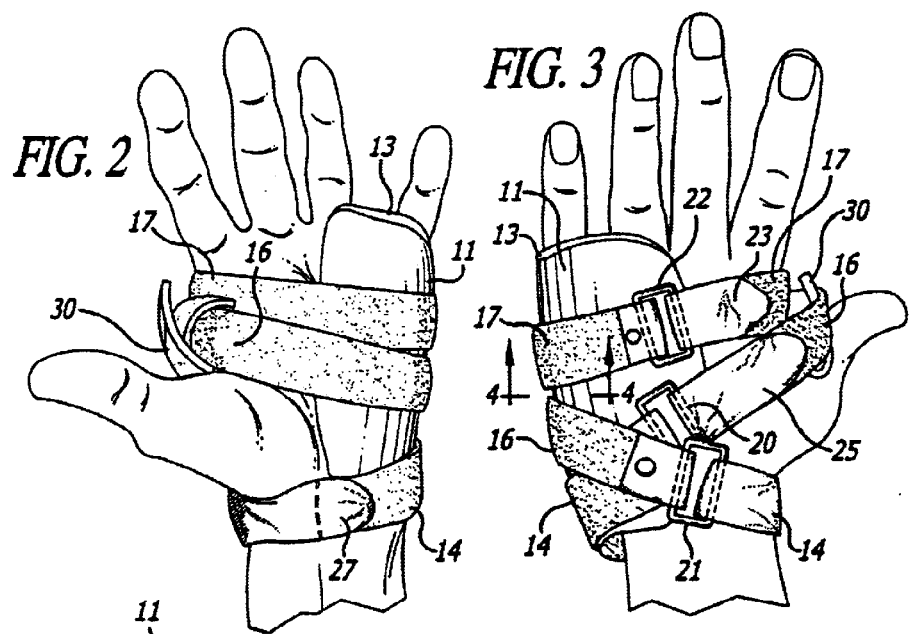
FIG. 2 is a reduced front elevational view illustrating the rigid fracture brace held in position on the hand of the user by the necessary three-strap assembly.
FIG. 3 is a view similar to the view in FIG. 2 illustrating the back of the rigid fracture brace when worn by the user.

It is noted in FIGS. 2 and 3 that the thumb strap 14 is trained from one rung of the loop 20 around the lower palm and immediately below the thumb of the wrist of the user, so that its free end and component 27 can be passed through the rung of loop 21 and folded over upon itself for securement with the second fastener component 28. The thumb strap 14 does not cross the wrist. In a similar fashion, the mid or palm strap 16 is trained from one rung of the loop 21 and is fastening rivet 15 around the back of the member 11 and across the palm, as shown in FIG. 2, and having its terminating end with the first fastening component 25 inserted through and folded over the exposed rung of loop 20 so that it can be connected with the second component 26 of the fastening means. In a similar fashion, the upper strap 17 progresses from loop 22 across the palm of the user's hand immediately below the fingers as shown in FIG. 2 so that its terminating end with fastener 23 can be inserted through the loop 22 and folded over upon itself for connection to the second component 24 carried on the outside of the strap 17. When the strap assembly is fully connected, the brace member 11 is held in position on the ulnar side of the hand of the user and the fingers are totally exposed and permit limited movement.

It is essential that the low profile metacarpal fracture brace with a rigid layer or shell have at least three straps to ensure tight fit in order to maintain fracture alignment, i.e., hold the broken bones in place. Employing less than three straps, as disclosed in the prior art, would cause the brace to improperly function. Two straps allows for movement between the brace or splint and the user's hand.

The strap securement or buckling system requires a minimum of three straps in order to immobilize and to provide fixation of the brace to the member. The proximal two straps are essential in order to bracket the thumb and prevent brace migration or movement. The third, more distal strap, is necessary to hold the brace securely against the member. It is essential to note that this brace has fixed rivets (no pivoting) which makes for a secure and immobile fixation of the brace.

Referring now to FIG. 4, it can be seen that the member 11 includes a rigid outside layer or shell 12 having an inner soft or cushioned layer 13. When carried on the hand of the user, the rigid member is particularly useful in immobilizing the fifth metacarpal which is indicated by numeral 31.

Figure 5:
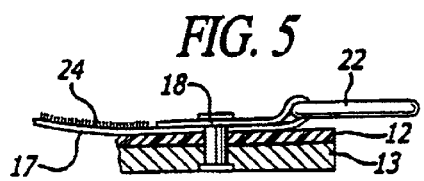
FIG. 5 is an enlarged view of the rigid fracture brace shown in FIG. 1 illustrated in the direction of arrows 5—5 thereof.

FIG. 5 illustrates the strap 17 as having the second component 24 covering the entire outside length of the strap which terminates,in the free end carrying the first component 23. Also, it can be seen that the strap is held on to the brace member or shell 11 by means of a non-pivoting and immobile rivet 18 after the end of the strap has been folded through one rung of the loop 22. A similar connection and construction is provided for straps 14 and 16 respectively.

The inventive brace 11 includes an elongated rigid and non-bendable layer or shell 11 that encompasses, not only the firth, but also the fourth, metacarpal phalangeal joint, which is not achieved by the prior art splints. The brace 11 allows freedom of wrist motion since no wrist strap is used. Brace 11 provides a linear shaped layer or shell having a high aspect ratio providing lengthwise support. The U-shaped layer or shell is held by the straps directly over the fracture site and ulnar side of the hand, leaving large portions of the user's palm and hand free for usage. Brace 11 must cover the fourth and fifth metacarpal phalangeal joints. Brace 11 is constructed of a rigid, non-bendable elongated member having an elongated, rigid outer layer or shell 12 defining an open-ended lateral cavity for receiving and supporting the user's hand encompassing the fourth and fifth metacarpal bones including and extending past the fourth and fifth metacarpophalangeal (MP) joints. It is critical that the brace extend past the MP joint to support the fracture and prevent deleterious motion at the metacarpal fracture site.

In view of the foregoing, it can be seen that the present invention provides a low profile metacarpal fracture brace which is designed to immobilize fractures of the fourth metacarpal and particularly the fifth metacarpal. The brace and strap assembly wraps around the ulnar side or border of the hand to approximately the middle of the hand on both palmar and dorsal surfaces. The brace extends from the base of the hypothenar eminence to beyond the fifth metacarpal-phalangeal joint to support the base of the proximal phalanx of the fifth finger. Brace position is maintained by the strap assembly running transversely around the hand. The brace may be manufactured in a variety of sizes as an ambidextrous construction allowing the brace to be worn on either hand. The brace can also be made specifically for right or left-sided wearing. The brace can be lined with either a soft gel-type padding or can be worn over a cloth stockinette material.

The profile metacarpal fracture brace is much easier and convenient for a physician to apply than other traditional methods of treating fourth and fifth metacarpal fractures such as casts or splints. The compact design allows more freedom of motion of the fingers than those other techniques thereby decreasing the likelihood of joint stiffness. The low-profile allows the brace to be used in active lifestyles and is particularly suited to be worn in sporting and industrial settings. Furthermore, the fracture brace is readily removable by the patient for bathing purposes.

Referring to FIGS. 6–7 inclusive, another embodiment of the invention is illustrated which is substantially similar to the embodiment shown in FIGS. 1–5 inclusive. The brace is indicated in the general direction of arrow 40 and includes a rigid and non-bendable layer or shell 41 which is U-shaped in cross-section and includes an open-ended cavity as well as a lateral opening leading into the cavity. The opening defines an entrance, such as indicated by numeral 41 in FIG. 11, and it can be seen that an inner cushion is provided, adjacent to the inside surface of the shell 41, as indicated by numeral 42. A minimum three straps, indicated by numerals 43, 44 and 45, are included and are similar to the straps and shell shown in FIG. 1. It is to be particularly noted that the one end of each strap is fixly secured to the rigid shell 41, such as by fasteners 46, 47 and 48. These fixed securements which are immobilized are shown in FIG. 7, while fasteners 50, 51 and 52 are shown in FIG. 8, and are immobile and non-pivotal. These latter fasteners connect the respective loops, such as loop 54, through which the respective straps are inserted and folded over upon themselves for fastening by hook and pile fastening arrangement as previously described. The hook and pile fastening arrangement is shown in FIG. 9, with the end of each strap passed through the respective loops and folded over, so that the two-component fastener can be merged into a releasable closure.

In FIGS. 6–10 inclusive, it can be seen that the shell 41 is rigid and non-deformable and that the length of the shell is of a high aspect ratio wherein the width of the shell is substantially less in dimension than the length of the shell. This permits the shell to completely cover the fracture site at the ulnar portion of the user's hand, while the fourth and fifth metacarpals are completely covered. In this embodiment, the cushion member 30 is not employed and is deemed unnecessary for this embodiment.

As previous described with respect to the embodiment shown in FIGS. 1–5, the inventive orthosis employing the brace is most useful when applied to fourth and fifth metacarpal fractures, especially the fracture known as "Boxer". The brace or orthosis is, applied as soon as the acute swelling subsides in the user's hand when there is appropriate clinical stability at the tissue site. In general usage, this means the brace is best applied about half to two-thirds of the way through the healing process. The orthosis is pre-formed and is rigid and non-bendable in usage, and the orthosis is held and stabilized in place with the three straps positioned on the palmar side and the thenar eminence relief situated towards the wrist. The palmer trim lines are wide over the MP joints and cut back away from the thenar eminence of the thumb. The elastic hook and pile fastener strap attached to the loops are on the dorsal side of the orthosis whereby the dorsal trim lines are semi-circular and symmetrical in shape. All of the straps are adjusted for a snug fit but not so tight as to hinder circulation or healing.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A rigid, non-bendable, low profile metacarpal fracture brace comprising:
   a U-shaped member having a rigid, non-bendable in use, outer layer defining an open-ended cavity having a lateral entrance for insertably receiving and supporting the ulnar portion of a user's hand adjacent to the metacarpal grouping of hand bones;
   at-least three straps having one end of each strap fixly and non-pivotally secured to said rigid member with an opposite end of each strap terminating in a free end;
   a buckling system carried on each of said ends of said straps secured to said member for insertably receiving said free ends;
   a releasable securement fastener carried on said straps for securing said member to the hand of the user;
   said three straps include a lower thumb strap, a middle palm strap and an upper palm strap;
   said member having a rigid front'side partially covering the palm of the user's hand and a rigid backside partially covering the back of the user's hand with a curved, rigid, non-bendable section joining said front side and said backside so that said U-shaped member is defined;
   said one end of each of said straps fixly secured to said backside;
   said three straps wrap transversely around the user's hand.

2. The fracture brace defined in claim 1 wherein:
   said member includes an inner surface and an outer surface; and
   a cushion material carried on said inner surface immediately adjacent to the hand of the user.

3. The fracture brace defined in claim 2 wherein:
   said member having a high aspect ratio and is held by said straps so as to extend from the base of the hypothenar eminence to beyond the fifth metacarpal-phalangeal joint of the user's hand to support the base of the proximal phalanx of the fifth finger.

4. The fracture brace defined in claim 3 wherein:
   said securement fastener includes a two-component hook and pile fastener carried on each of said straps respectively avoiding prior necessity of registering of fastener components.

5. The fracture brace defined in claim 4 wherein:
   said one end of each of said straps includes a loop for accommodating insertion of said free end for folding over upon itself to couple said two component hook and pile fastener.

6. A low profile metacarpal fracture brace worn on a hand of a user comprising:
   an elongated member of U-shaped cross-section and of a high aspect ratio and having an internal recess with an upper and lower opposite open ends joined by a lateral entrance leading into said internal recess;
   said member composed of a hard, rigid, and non-bendable composition providing a rigid shell having a top section adjacent the back of the user's hand when worn by the user, an under section adjacent the palm of the user's hand when worn by the user and an arcuate section joining said top section with said under section, cooperating to define said recess;
   said rigid shell having an outer surface and an inner surface;
   a cushion material secured to said rigid shell inner surface;
   an elongated strap means having a first end secured to said outer surface of said shell and a second end terminating in a free end with a mid-section integrally connecting said first And with said second end;
   said first end of said strap means having at least one loop permitting insertion of said free end therethrough for folding over upon itself allowing said free end to overlap against said mid-section;
   a two-component fastener means carried on said free end and said mid-section respectively for releasably connecting said strap means;
   said strap means being wrapped transversely about said rigid shell and the hand of the user when said member is worn by said user;
   said strap means includes at least three elongated straps;
   a first and a second strap of said strap means fixly and immovably secured to said rigid shell immediately adjacent to said lower end in fixed spaced-apart relationship constituting a lower thumb strap and a mid-strap respectively;
   a third strap of said strap means fixly and immovably secured at its one end to said shell immediately adjacent to said upper end thereof constituting a finger strap;
   said mid-strap and said finger strap adapted to wrap about the user's hand across the user's palm and between the user's thumb and index finger with said thumb strap adapted to wrap about the lower portion of the user's thumb.

7. The fracture brace defined in claim 6 including:
   a spaced area of soft composition carried on said mid-section of said mid-strap for positioning between the thumb and index finger of the user.

8. The fracture brace defined in claim 7 wherein:
   said fastener means is of a non-registerable type and includes a hoop and pile fastener on each of said straps of said strap means.

9. The fracture brace defined in claim 8 wherein:
   said rigid member insertably receives a portion of the user's hand in said recess whereby said member extends from the base of the hypothenar eminence to beyond the fifth metacarpal-phalangeal joint to support the base of the proximal phalanx of the fifth finger.

10. The fracture brace defined in claim 9 wherein:
    said member and said shell are stiff, hard, rigid and non-bendable in use so as to avoid deformation during application of said member and said shell onto a user's's hand;

said straps wrap transversely around the user's hand;

said rigid U-shaped member includes an inner surface and an outer surface;

a cushion material carried on said inner surface immediately adjacent to the hand of the user and conformal therewith;

said rigid U-shaped member is held by each of said three straps so as to extend from the base of the hypothenar eminence of the hand to beyond the fifth metacarpal-phalangeal joint of the user's hand to support the base of the proximal phalanx of the fifth finger;

said securement fastener includes a two-component hook and pile fastener carried on each of said straps respectively; and said one end of each of said three straps includes a loop for accommodating insertion of said free end therethrough for folding over upon itself to couple said two-component hook and pile fastener.

11. A low profile metacarpal fracture brace worn on the hand of a user comprising:

an elongated rigid, non-bendable member of U-shaped cross-section having an internal recess with upper and lower open opposite ends joined by a lateral entrance leading into said internal recess;

said member composed of a hard and rigid composition providing a rigid, stiff and immobile shell having a rigid back section adjacent to and extending partially across the back of the user's hand when worn by the user, a rigid palm section adjacent to and extending partially across the palm of the user's hand when worn by the user and a rigid arcuate mid-section joining said rigid back section with said rigid palm section cooperating to define said recess;

said rigid shell having an outer surface and an inner surface;

a cushion material secured to said shell inner surface;

a set of three elongated straps having a first end of each strap fixly and immovably secured to said outer surface of said rigid shell and a second end terminating in a free end with a mid-section integrally connecting said first end with said second end;

at least three loops fixly secured to said shell permitting insertion of said free ends of said straps therethrough for folding over upon themselves allowing said free ends to overlap against said mid-section of each strap respectively;

a two-component hook and pile fastener means carried on said free end and said mid-section respectively for releasably connecting said strap means;

said set of straps being wrapped transversely about said shell and the hand of the user when said member is worn by said user;

a first and a second strap of said set of straps fixly secured to said shell immediately adjacent to said lower end thereof constituting a behind-the-thumb strap and a mid-strap respectively;

a third strap of said set of straps fixly secured at its one end to said shell immediately adjacent to said upper end thereof constituting a finger strap; and said mid-strap and said finger strap adapted to wrap about the user's hand across the user's palm and between the user's thumb and index finger with said behind-the-thumb strap adapted to wrap about the thumb of the user.

* * * * *